United States Patent [19]

Strong

[11] Patent Number: 4,978,530

[45] Date of Patent: Dec. 18, 1990

[54] SANITIZED, DISINFECTED AND SPORICIDAL ARTICLES, AND PROCESSES FOR SANITIZING, DISINFECTING AND RENDERING OBJECTS SPORICIDAL

[75] Inventor: Frank Strong, Mississauga, Canada

[73] Assignee: Health Care Products, Inc., Mississauga, Canada

[21] Appl. No.: 18,516

[22] Filed: Feb. 25, 1987

Related U.S. Application Data

[63] Continuation-in-part of Ser. No. 858,816, May 2, 1986.

[51] Int. Cl.$^5$ .................. A01N 25/34; A01N 35/00; A01N 35/02
[52] U.S. Cl. ............................ 424/413; 424/412; 514/695; 514/698; 514/705
[58] Field of Search .................. 514/698, 695, 705; 424/445, 446, 447; 604/304, 412, 413

[56] References Cited

U.S. PATENT DOCUMENTS

| | | | |
|---|---|---|---|
| 1,741,668 | 12/1929 | Wilson | 379/450 |
| 2,359,240 | 9/1944 | Partansky | 424/128 |
| 3,016,328 | 1/1962 | Pepper et al. | 424/127 |
| 3,282,775 | 11/1966 | Stonehill | 514/705 |
| 3,317,376 | 5/1967 | Schattner | 424/404 |
| 3,697,222 | 10/1972 | Sierra | 422/20 |
| 3,708,263 | 1/1973 | Boucher | 422/20 |
| 3,912,450 | 10/1975 | Boucher | 422/20 |
| 3,917,850 | 11/1975 | Boucher | 514/705 |
| 3,968,248 | 7/1976 | Boucher | 514/705 |
| 3,968,250 | 7/1976 | Boucher | 514/705 |
| 3,983,252 | 9/1976 | Buchalter | 514/698 |
| 3,991,124 | 11/1976 | Schellenbaum | 424/78 |
| 4,048,336 | 9/1977 | Winicov et al. | 514/694 |
| 4,069,307 | 1/1978 | Higuchi et al. | 424/432 |
| 4,093,744 | 6/1978 | Winicov et al. | 514/705 |
| 4,103,001 | 7/1978 | Schattner | 424/148 |
| 4,436,754 | 3/1984 | Jacobs | 514/694 |
| 4,446,967 | 5/1984 | Halkyard | 206/368 |
| 4,469,614 | 1/1984 | Martin | 514/705 |

OTHER PUBLICATIONS

Chem. Abst. 81:137862z, (1974)—Moerikofer.
Chem. Abst. 84:8947n, (1976)—Walliczek.

Primary Examiner—Allen J. Robinson
Attorney, Agent, or Firm—Sandler, Greenblum & Bernstein

[57] ABSTRACT

A process for sanitizing, disinfecting, and killing spores involves providing a tangible object made from polymeric material impregnated with an aqueous glutaraldehyde solution which is packaged in an air-tight enclosure, removing the impregnated tangible object from the enclosure, and applying the impregnated tangible object to the surface to be sterilized and/or sanitized and disinfected so as to expose spores, bacteria, virus, and other microorganisms present on the surface to the action of the glutaraldehyde solution. A sanitary attachment for a receiver or mouthpiece of a telephone made from plastic material incorporating a glutaraldehyde solution. A fabric made from cellulosic or plastic material having sporicidal and/or sanitizing and disinfectant activity as a result of being impregnated with a glutaraldehyde solution. A method for sanitizing and disinfecting and/or rendering fabric sporicidal involves impregnating a fabric with an aqueous glutaraldehyde solution prior to packaging the fabric in an air-impervious container until ready for use.

3 Claims, 1 Drawing Sheet

SANITIZED, DISINFECTED AND SPORICIDAL ARTICLES, AND PROCESSES FOR SANITIZING, DISINFECTING AND RENDERING OBJECTS SPORICIDAL

This application is a continuation-in-part application of U.S. patent application Ser. No. 858,816, filed on May 2, 1986.

BACKGROUND OF THE INVENTION

1. Field of the Invention

The present invention is directed, to sanitized, disinfected and sporicidal articles and methods for manufacturing such articles. More particularly, the present invention is directed to fabrics and plastic articles incorporating aqueous sanitizing, disinfecting and sterilizing compositions including glutaraldehyde. Specifically, the present invention is directed a sanitary attachment to be attached to a telephone receiver or mouthpiece formed from a plastic material and fabrics made from cellulosic or plastic materials incorporating aqueous sanitizing and disinfectant solutions including glutaraldehyde, sodium lauryl sulfate, glycerol, phenol, monosodium phosphate, and disodium phosphate. The present invention is also directed to methods for manufacturing the articles incorporating glutaraldehyde solutions and the method for sanitizing and disinfecting a contaminated surface using articles incorporating such glutaraldehyde solutions.

2. Discussion of Background and Material Information

In the past numerous compositions have been proposed for disinfecting or sterilizing a variety of objects. Formaldehyde is one of the oldest chemosterilizers employed for the destruction of spores. The fumes of formaldehyde, however, limit its usefulness and its toxicity for tissue requires that disinfected materials be thoroughly rinsed with sterile water before use. Recently, alkalinized glutaraldehyde solutions have become widely used for such purposes. Typically, they consist of an aqueous glutaraldehyde solution buffered by suitable alkalinating agents to a pH 7.5 to 8.5. In the acid state at room temperature, glutaraldehyde solutions are stable for long periods of time when stored in a closed container. When rendered alkaline, however, the glutaraldehyde gradually undergoes polymerization and loses its activity, which proceeds very rapidly above pH 9.

A buffered phenol-glutaraldehyde sterilizing composition which has met with wide acceptance is known commercially under the trade name Sporicidin and is the subject of U.S. Pat. No. 4,103,001. The aqueous sporicidal composition of U.S. Pat. No. 4,103,001 includes by weight from 0.75–4.0% glutaraldehyde and from 4–15% of a mixture of phenol and a metal phenate, the phenol content being from 3–10% and the metal phenate being from 0.5–5%, with the composition having ph of 7–10 and an active sterilizing life of at least 30 days. The sporicidal composition of U.S. Pat. No. 4,103,001 was formulated in an attempt to overcome the disadvantages, particularly the limited stability, of alkaline glutaraldehyde solutions. The buffered phenol-glutaraldehyde combination is normally used by applying the solution to the surface of the object to be sterilized.

Fabrics have been produced which exhibit anti-bacterial and germicidal properties, for example, by the process of U.S. Pat. No. 3,317,376 wherein fabrics are impregnated with an aqueous solution including from 0.8% to 15% by weight sodium phenolate, from 0.3% to 5.5% of sodium tetraborate, from 0.8% to 15% glycerine, from 2.0% to 16.5% of phenol and the balance water.

More recently, it has been suggested in U.S. Pat. No. 4,446,967 to impregnate a germicide enclosure for dental and medical instruments made of a relatively thick layer of compressible absorbent material, such as foamed plastic material, with Sporicidin being mentioned as a suitable germicide for this purpose.

U.S. Pat. No. 4,069,307 relates to a drug-delivery device for releasing a drug at a continuous and controlled rate for a prolonged period of time made from polymeric material such as an ethylene-vinyl acetate.

U.S. Pat. No. 3, 317,376 is directed to a process for impregnating or otherwise treating fabrics which are made from synthetic or natural fibers with an aqueous solution of 0.8% to 15% by weight of sodium phenolate, 0.3% to 5.5% by weight of sodium tetraborate, 0.8% to 15% by weight of glycerine, 2.0% to 16.5% by weight of phenol.

U.S. Pat. No. 1,741,668 is directed to a sanitary attachment made of porous material adapted to be connected to a telephone transmitter which is treated with a germicidal agent, such as formaldehyde.

In accordance with the present invention, glutaraldehyde solutions are impregnated into fabrics made from natural and synthetic materials which are formed into desired articles, such as sanitary towelettes and sanitary attachments for telephones, which are packaged in air-impervious containers until ready for use.

SUMMARY OF THE INVENTION

An object of the present invention is a process for sanitizing, disinfecting and killing bacterial, virus spores and other microorganisms which involves providing a tangible object made from polymeric material which is impregnated with an aqueous glutaraldehyde solution and packaged in an air-tight enclosure; removing the impregnated tangible object from the enclosure; and applying the impregnated tangible object to inanimate surfaces so as to expose bacteria, virus and spores present thereon to the action of glutaraldehyde. The polymeric material is preferably selected from the group consisting of cellulosic materials and plastic materials, such as an ethylene-vinyl acetate resin, with the tangible objects including appliances, bedding, cloths, clothing, containers, coverings, equipment, fabrics, flooring, garments, instruments, masks, towels, towelettes and utensils. Particularly preferred tangible objects for purposes of this process of the present invention are attachments to be connected to a telecommunication receiver or mouthpiece, and towelettes for wiping a contaminated object.

Another object of the present invention is to provide a sanitary attachment to be attached to a receiver or mouthpiece of a piece of telecommunication equipment, such as a telephone, including a body portion of plastic material incorporating a glutaraldehyde solution, and preferably also including a litmus base indicator, which is packaged in an air-impervious film.

A further object of the present invention is the provision of a fabric having sanitizing, disinfecting and sporicidal activity as a result of being impregnated with a glutaraldehyde solution, and preferably a litmus base indicator, which is packaged in an air-impervious container, wherein the fabric is made from a member selected from the group consisting of a cellulosic material and a plastic material.

Another still further object of the present invention is a method for sanitizing and disinfecting a fabric which involves impregnating fabric with an aqueous solution including glutaraldehyde prior to packaging the fabric in an air-impervious container until ready for use. The fabric is preferably also impregnated with an effective amount of a litmus base indicator.

The glutaraldehyde solutions which have been found to be effective for purposes of all embodiments of the present invention are aqueous solutions selected from the group of solutions consisting of solutions comprising glutaraldehyde, sodium lauryl sulfate glycerol, phenol, monosodium phosphate, and disodium phosphate, and solutions comprising glutaraldehyde and a mixture of phenol and metal phenate. More preferred glutaraldehyde solutions for purposes of the present invention are members selected from the group of solutions consisting of solutions comprising 0.005–0.30% glutaraldehyde, 0.1–0.3% sodium lauryl sulfate, 0.25–0.75% glycerol, 0.25–0.75% phenol, 0.01–0.03% monopotassium phosphate, and 0.1–0.12% disodium phosphate, and solutions comprising 0.75–4.0% glutaraldehyde and from 4–15% of a mixture of phenol and metal phenate, with the phenol content being from 3–10% and the metal phenate being from 0.5–5% by weight of said aqueous solution.

The most preferred solution for purposes of the present invention comprises 0.75–0.15% glutaraldehyde, 0.25% sodium lauryl sulfate, 0.5% glycerol, 0.5% phenol, 0.03% monopotassium phosphate, and 0.108% disodium phosphate.

DETAILED DESCRIPTION

Figure 1:
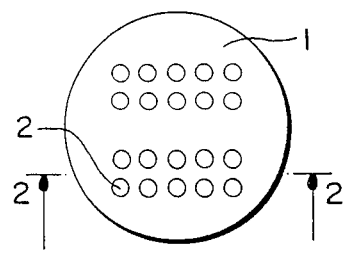
FIG. 1 is a plane view of a telephone disk for attachment to a telephone transmitter or receiver.

In accordance with the present invention, it has been discovered that numerous items, including fabrics and plastic articles, may be impregnated with solutions comprising glutaraldehyde, sodium lauryl sulfate glycerol, phenol, monosodium phosphate, and disodium phosphate and solutions comprising glutaraldehyde and a mixture of phenol and metal phenate, to render them sporicidal and/or sanitized and disinfected for extended periods of time. As previously mentioned, solutions including glutaraldehyde have been found to be very effective against a wide variety of micro-organisms including virus, such AIDS and Herpes. Although articles and fabrics made from cellulosic and plastic material have been impregnated with a variety of active agents, including germicidal solutions, so as to deliver the active agent to a desired target over a prolonged period of time, it is not believed that aqueous glutaraldehyde solutions comprising glutaraldehyde, sodium lauryl sulfate glycerol, phenol, monosodium phosphate, and disodium phosphate and aqueous solutions comprising glutaraldehyde and a mixture of phenol and metal phenate have been effectively used for this purpose. Notwithstanding the improvements made to the storage stability of glutaraldehyde solutions as set forth in U.S. Pat. No. 4,103,001, even Sporicidin lacks the proper storage stability when exposed to the atmosphere to be generally useful in delayed delivery systems. In accordance with the present invention, therefore, articles incorporating aqueous glutaraldehyde solutions comprising glutaraldehyde, sodium lauryl sulfate glycerol, phenol, monosodium phosphate, and disodium phosphate and aqueous solutions comprising glutaraldehyde and a mixture of phenol and metal phenate are individually packaged in air-tight containers and stored until ready for use. As desired, the particular article is then removed from its air-tight container and used in accordance with the particular application for which it was intended.

The present invention may make use of any of the commercially available glutaraldehyde solutions, such as those which are currently marketed under the brand names Cidex, Sonacide, Sporicidin and Ucarcide.

Of the previously mentioned commercially available glutaraldehyde solutions, a glutaraldehyde solutions which function effectively as a cold sterilizing agent for purposes of the present invention include buffered phenolglutaraldehyde sterilizing compositions made in accordance with U.S. Pat. No. 4,103,001. Sporicidin has been found to be particularly effective for purposes of the present invention because it exhibits a pH of about 7–10 and an active sterilizing life of at least 30 days. The glutaraldehyde solution commercially sold as Sporicidin is an aqueous composition containing from 0.75–4.0% glutaraldehyde and from 4–15% of a mixture of phenol and a metal phenate, with the phenol content being from 3–10% and the metal phenate being from 0.5–5% by weight of the composition. The composition preferably also includes 1–5% by weight of sodium tetraborate and preferably at least one anionic or nonionic surfactant, which may be selected from the group consisting of sodium dodecyl benzene sulphonate and sodium cocoyl sarcosinate, preferably in the amount of 2–10% by the weigh of composition, as well as a humectant, selected from the group consisting glycerol di-ethylene glycol and propylene glycol. The preferred ratio of phenol to sodium phenate in the aqueous composition is 5–7 to 1.

Glutaraldehyde solution which are more preferred for sanitizing and disinfecting purposes, however, are aqueous solutions comprising 0.005–0.30% glutaraldehyde, 0.1–0.3% sodium lauryl sulfate, 0.25–0.75% glycerol, 0.25–0.75% phenol, 0.01–0.03% monopotassium phosphate, and 0.1–0.12% disodium phosphate, and most preferably solutions comprising 0.75–0.15% glutaraldehyde, 0.25% sodium lauryl sulfate, 0.5% glycerol, 0.5% phenol, 0.03% monopotassium phosphate, and 0.108% disodium phosphate with the balance being water.

The present invention finds utility with respect an almost limitless variety of products, including fabric items made from natural and synthetic material, and articles made from plastic materials. In this regard, the fabrics which may be used in accordance with the present invention include non-woven and woven fabrics, including those made from natural materials such as paper or other cellulosic materials, cotton, wool, and blends thereof, as well as synthetic materials such as nylon, rayon, acrylics, and the like. It is preferred, however, to use a fabric made from cellulosic materials for purposes of the present invention. The plastics which may be used to form the sheeted, molded or extruded articles incorporating glutaraldehyde in accordance with the present invention may be selected from conventional plastic materials which have been found to be acceptable for use in the delayed-delivery systems. Plastic material which may be used in the present invention include flexible plastics, such as polyvinyl chloride, or low density polyethylene, in addition to an ethylene-vinyl acetate copolymer resin, such as commercially available Dupont EVA 3185. This ethylene-vinyl acetate copolymer resin exhibits the following physical characteristics: melt index of 43 decigrams/min., ASTM D-1238, weight % vinyl acetate 33, and a density of 960 kg/m$^3$ (0.96 gm/cc ACTM D-792).

The fabric to be treated is preferably cut into sections of any desired size, such as twelve inch squares, which are impregnated with a gluteraldehyde solution. In the embodiment where Sporicidin is used, the Sporicidin is diluted with water. It is preferred to dilute commercial-strength Sporicidin with water in a ratio which falls within the range of 1:12–30. Particularly preferred results are achieved when Sporicidin is diluted with water in the ratio of 1:12.5, 1:16, 1:30. The other glutaraldehyde solutions which have previously been mentioned, however, may be used without further dilution with water. The sections of fabric may be impregnated with the glutaraldehyde solutions by any means which assures complete saturation of the fabric with the solution, including spraying the fabric or immersing the fabric in a bath of the solution. After impregnation, the sections of fabric may be further reduced in size, separated into individual sheets and packaged in a suitable container which seals the fabric from the atmosphere.

Although any type of container or package which would effectively protect the impregnated fabric from exposure to air from the surrounding environment can be used, plastic films made from polyvinyl chloride, polyethylene and the like which have been processed to render them substantially air-tight or air-impervious are more suitable for this purpose. A plurality of the individually packaged fabric sheets are then assembled in a packet, package or other container for storage, shipping, handling and distribution.

In order to render a surface of an object sporicidal, and/or sanitize and disinfect the object, the end user takes one of the individually wrapped sheets of fabric, removes the protective film from the glutaraldehyde-impregnated sheet of fabric and wipes or otherwise contacts the surface of the object which may be contaminated with the Sporicidin-impregnated fabric so as to kill any spores and/or bacteria, virus and other microorganisms which may be present on the surface of the object.

Another preferred article made and used in accordance with the present invention is a sanitary attachment for a telephone transmitter or receiver. The concern for providing an effective sanitary attachment for telephones has existed almost since the telephone was first invented. As one can appreciate, the mouthpiece of a telephone is prone to be contaminated with numerous germs as a result of being brought close to the mouth of the user. Accordingly, numerous devices have been developed in an attempt to sanitize or otherwise disinfect the mouthpiece of telephones to kill bacteria and germs which may be responsible for illness and diseases, such as the common cold, flu and the like. In recent years, however, there has been a heightened concern for protection against virus, such as AIDS and Herpes, which are believed to be spreading at a rapid rate. Inasmuch as glutaraldehyde solutions such as Sporicidin, are among the few germicidal solutions effective against AIDS and Herpes, the present invention finds particularly utility in the production of articles incorporating glutaraldehyde solutions which have been formed into attachments for a telephone mouthpiece to effectively protect the user from essentially all types of bacterial, virus and other microorganisms.

Figure 2:
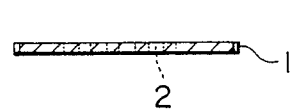
FIG. 2 is a cross-section view of the telephone disk of FIG. 1 taken along line II—II.

A sanitary telephone attachment made in accordance with the present invention is generally shown in FIGS. 1 and 2 in the attached drawings. As shown, the sanitary telephone attachment has been formed in the shape of a disk having a body portion 1 made of plastic material, such as polyvinyl chloride, low density polyethylene, or ethylene-vinyl acetate resin. The disk is shown as being provided with a number of orifices 2 so as not to mute the transmission of sound through the disk, and any number or arrangement of orifices which is effective for this purpose may be provided in the telephone disk of the present invention. Although the plastic material may be sheeted, cut into the desired shape and perforated, it is preferred to extrude the plastic material through a die plate suitable for imparting the desired disk-shape with a suitable arrangement of orifices.

A procedure for producing a sanitary telephone attachment for purposes of the present invention will now be described. Initially, 99 parts of an ethylene-vinyl acetate resin are combined with one part of Sporicidin diluted with water in a ratio of 1:12.5, 1:16, 1.30. In addition, an effective amount of a litmus base indicator was also included in the mixture. The foregoing materials were then tumble-blended without heating for about 5 minutes to achieve optimum dispersion of the solution within the plastic material to produce a base blend or mixture of ethylene-vinyl acetate incorporating Sporicidin. The base blend or mixture was then extruded using a standard one inch single screw extruder exhibiting a heat profile ranging from 250° F. at the feed throat to 300° F. at the die plate to result with an elongate extrusion or piece. The extruded material was then cooled in a water bath prior to drying to render it suitable for subdividing into pellets. The pellets of ethylene-vinyl acetate resin incorporating Sporicidin solution where then blended with a batch of ethylene-vinyl acetate resin in a ratio of 1:9 to produce and extrudable admixture or mass which was then passed through an extruder and cut into disks having the size and arrangement of orifices as shown in FIG. 1. The sanitary telephone disks incorporating Sporicidin where then individually sealed within two layers of an air-impervious plastic material, such as polyethylene, and assembled into an appropriate packet or other suitable container for shipping, storage, handling and distribution.

Figure 3:
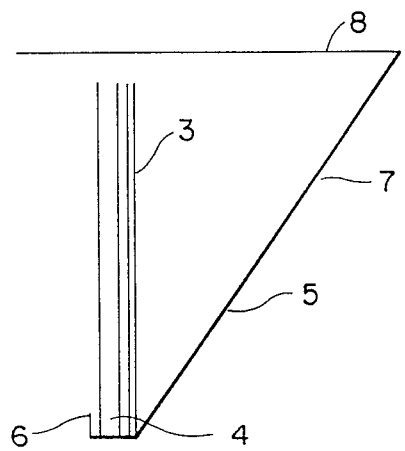
FIG. 3 is a side view of a package containing articles made in accordance with the present invention.

A preferred packet for storing a plurality of individually packaged articles made in accordance with the present invention is generally illustrated in FIG. 3. As shown, the individual articles incorporating a glutaraldehyde solution are packaged within air-impervious films 3. The individual enclosures for the impregnated articles are connected together at one end 4 by glue, staples or merely being heat sealed, in addition to being fastened within a protective packet or container 5 until ready for use. A particularly suitable packet is one similar to a match book cover having generally U-shaped end 6 wrapped around the lower ends 4 of the individual containers for the articles in such a way as to secure them to the packet which also includes a back side 7 and front side 8 adapted to fold over and engage end 6 to protect the plastic film packaged articles from damage.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A package article having santizing and disinfecting properties comprising fabric impregnated with an aqueous gluaraldehyde solution consisting essentially of 0.005–0.30% glutaraldehyde 0.1–0.3% sodium lauryl sulfate, 0.25–0.75% glycerol, 0.25–0.75% phenol, 0.01–0.03% monopotassium phosphate, and 0.1–0.12% disodium.

2. The packaged article of claim 1, wherein said fabric is a material selected from the group consisting of a cellulosic material and a plastic material.

3. The packaged article of claim 1, wherein said fabric is impregnated with a litmus base indicator.

* * * * *